United States Patent [19]

Cole et al.

[11] 4,347,314

[45] Aug. 31, 1982

[54] PROCESS FOR THE PREPARATION OF PENICILLIN DERIVATIVES

[75] Inventors: Martin Cole; Robert A. Edmondson, both of Dorking, England

[73] Assignee: Beecham Group Limited, England

[21] Appl. No.: 149,342

[22] Filed: May 13, 1980

[30] Foreign Application Priority Data

May 15, 1979 [GB] United Kingdom ............... 7916773

[51] Int. Cl.$^3$ ............................................ C12P 37/00
[52] U.S. Cl. .................................... 435/43; 260/239.1
[58] Field of Search ....................... 435/43; 260/239.1

[56] References Cited

U.S. PATENT DOCUMENTS 3,528,965  9/1970  Cole et al. ............................. 435/43

FOREIGN PATENT DOCUMENTS 1160211  8/1969  United Kingdom .
1264147  2/1972  United Kingdom .

*Primary Examiner*—Natalie Trousof
*Assistant Examiner*—Vera C. Clarke
*Attorney, Agent, or Firm*—Jacobs & Jacobs

[57] ABSTRACT

A process for the preparation of α-carboxy, 6, α-methoxy penicillin derivatives by the enzymatic hydrolysis of an esterified derivative.

The process is for the preparation of a compound of formula (I):

$$\text{R.CH.CO.NH} \overset{\text{OCH}_3}{\underset{\text{CO}_2\text{H}}{|}} \begin{array}{c} \text{S} \\ \text{N} \end{array} \diagdown \text{CO}_2\text{H} \qquad (I)$$

wherein R represents phenyl or 2- or 3-thienyl, which process comprises subjecting a compound of formula (IV):

$$\text{R.CH.CO.NH} \overset{\text{OCH}_3}{\underset{\text{CO}_2\text{R}^1}{|}} \begin{array}{c} \text{S} \\ \text{N} \end{array} \diagdown \text{CO}_2\text{H} \qquad (IV)$$

where R$^1$ is an aryl radical, to the action of an enzyme selected from bromelain, papain, gelatase, trypsin, pancreatin or an esterase-producing strain of *Escherichia coli*, *Pseudomonas aeruginosa*, *Aspergillus niger* or *Saccharomyces sp.*

7 Claims, No Drawings

PROCESS FOR THE PREPARATION OF PENICILLIN DERIVATIVES

This invention relates to a process for the preparation of penicillin derivatives and in particular to the preparation of α-carboxy, 6, α-methoxy penicillin derivatives by the enzymatic hydrolysis of an esterified derivative.

The compounds prepared by the process of this invention have the formula (I):

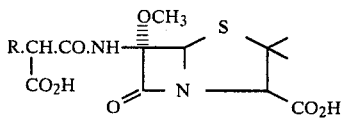
(I)

wherein R represents phenyl or 2- or 3-thienyl. Our British Patent No. 1,538,052 discloses compounds of formula (I) wherein R is 2- or 3-thienyl and the compound of formula (I) wherein R represents phenyl is disclosed in British Patent No. 1,339,007.

One method for the preparation of compounds of formula (I), which is disclosed (for the R=thienyl compounds) in British Patent No. 1,538,052, comprises reacting a compound of formula (II):

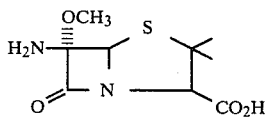
(II)

with inter alia an N-acylating derivative of an acid of formula (III):

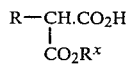
(III)

wherein $R^x$ is a carboxyl blocking group, and subsequently removing the group $R^x$. We have now found that ester groups at the α-position can be converted to the free acids by the action of certain enzymes.

The enzymatic hydrolysis of certain α-esters of α-carboxy, 6-H penicillins is disclosed in British Patent No. 1,160,211. However, the 6-methoxy derivatives of formula (I) above represent a completely different class of compounds and it is not possible to predict whether the enzymes disclosed in Patent No. 1,160,211 would hydrolyse α-esters of compounds (I) above. In fact some of the enzymes disclosed in Patent No. 1,160,211 are not useful for preparing compounds of formula (I), one such example being Sepedonium sp.

Accordingly the present invention provides a process for the preparation of a compound of formula (I):

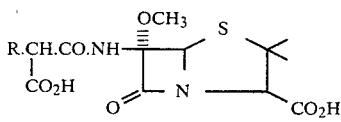
(I)

wherein R represents phenyl or 2- or 3-thienyl, which process comprises subjecting a compound of formula (IV):

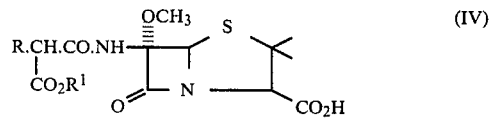
(IV)

where $R^1$ is an aryl radical, to the action of an enzyme selected from bromelain, papain, gelatase, trypsin, pancreatin or an esterase-producing strain of *Escherichia coli*, *Pseudomonas aeruginosa*, *Aspergillus niger*, or *Saccharomyces* sp.

Suitable aryl groups $R^1$ include phenyl or substituted phenyl wherein the substituent is at least one of chloro, bromo, fluoro, $C_{1-6}$ alkyl, $C_{1-6}$ alkoxy, $C_{1-6}$ alkanoyl, $C_{1-6}$ alkoxycarbonyl, nitro or di-($C_{1-6}$)alkylamino.

Preferred aryl groups $R^1$ include phenyl, and mono-, di- and tri-($C_{1-6}$)-alkyl substituted phenyl such as o-m-, or p-methylphenyl, ethylphenyl, n- or iso-propylphenyl, or n-, sec-, iso- or t-butylphenyl.

Suitable esterase forming strains of the above mentioned microorganisms and moulds include *E. coli* K12 (NCIB 10112) and BRL 1873 (ATCC 9723), *Ps. aeruginosa* A (NCIB 10110) and R59 (NCIB 10111) *Aspergillus niger* BRL 822 (IMI 130783), *Saccharomyces cerevisiae* BRL BRL 611, *Saccharomyces carlsbergensis*, BRL 622.

A preferred esterase is that produced by *Aspergillus niger*.

The esterase enzyme can be prepared by culturing the microorganism or mould in a conventional manner, especially under aerobic conditions in a suitable liquid or semi-solid media. In general, carbon and nitrogen sources which microorganisms can assimilate and inorganic salt nutrients essential for the growth of the microorganisms are included in the culture medium. The culture conditions may be a temperature of from 20° C. to 80° C. and a pH of from 4 to 11. Preferred conditions are 20° C. to 30° C. at a pH of 5 to 9, suitably about pH7, for 1 to 10 days. The cultured microorganism containing the esterase is employed for the process of this invention in the form of the cultured broth, separated cells, or isolated enzyme.

When bromelain, papain, gelatase, trypsin or pancreatin is employed as the esterase enzyme for the process of this invention, the enzyme may be employed itself or attached to an insoluble support either by adsorption, for example as disclosed in British Patent No. 1,264,147, or by covalent bonds either directly or indirectly via bridging groups, for example as described in British Patent Nos. 1,349,498, 1,387,460 and 1,365,886. Alternatively, the enzyme may be bound to a water soluble polymeric support (see British Patent Nos. 1,284,925 and 1,449,808) so that the enzyme/polymer complexes are recoverable from the aqueous reaction mixture by ultrafiltration; or the enzyme may be attached to non-polar groups (and optionally polymeric supports) as described in British Patent No. 1,463,513, to render the preparation separable from aqueous media by virtue of the affinity for water-immiscible liquids.

The hydrolysis reaction of the present invention is generally carried out in aqueous media, the reaction mixture being maintained in the range pH5 to 9 and preferably about pH7. The pH is controlled either by using buffers or by continuous addition of aqueous alkali metal hydroxide until reaction is complete. The temperature of the reaction should be suitable for the enzyme employed and is generally in the range 20° C. to 50° C. preferably 30° C. to 40° C. The reaction time depends on such factors as concentrations of reactants, temperature and pH. After the reaction is complete the reaction mixture is acidified and the penicillin derivative of formula (I) isolated by conventional methods. It is usually convenient to precipitate the compound (I) as an alkali metal salt, for example the disodium salt.

This invention is illustrated by the following assays.

ASSAY METHOD

The compound of formula (I) wherein R is 3-thienyl will be referred to herein as compound AB17421. In order to illustrate the rate of hydrolysis of esters of compound AB17421 by a number of enzymes according to this invention, esters were subjected, in aqueous reaction mixtures, to the action of the particular enzyme and the percentage of hydrolysis of the ester was determined after time intervals using the following assay method:

5 μl samples are removed from the reaction mixtures and spotted on to Whatman No. 1 chromatography tapes 1 cm wide. 5 μl samples of standard solutions of AB 17421 are spotted on to separate tapes. The tapes are developed by descending chromatography using butanol/ethanol/water (4:1:5 top phase) for 16 hours and dried thoroughly. [AB17421 runs very close to the origin (Rf=0.035) whilst the esters generally run much nearer the solvent front in this solvent.] A section of tape 10 cm long, including 2 cm behind the origin, is cut off and placed in contact with Blood Base Agar (Oxoid) CM55 seeded with *Escherichia coli* ESS, a sensitive mutant. The plates are incubated at 37° C. for about 5 hours then overnight at 28° C. The diameters of the zones of inhibition are measured and the percentage conversion to AB17421 is calculated with reference to the standard line of diameter of antibiotic zone against the log of the concentration.

Assay 1

De-esterification of α-(p-methylphenyl) ester of AB17421 by esterase from *Escherichia coli*

(a) Cultivation

Two strains of *Escherichia coli* (K12, NCIB 10112 and BRL 1873, ATCC 9723) were grown in 2.5% Nutrient Broth No. 2 (Oxoid) at 37° C. for 16 hours.

(b) Hydrolysis Reaction

Incubation mixtures were then set up containing a 1:1 v/v mixture of 8 mg/ml p-methylphenyl ester of AB17421 dissolved in 0.05 M potassium phosphate buffer, pH 7.0 and whole bacterial culture. The reaction mixtures were incubated at 37° C. with occasional shaking. Controls were set up in which 0.05 M potassium phosphate buffer was used in place of the bacterial culture. The formation of AB17421 was determined as in the assay method above. The percentages of hydrolysis of the ester after 3 hours and 6 hours are given in Table 1.

TABLE 1

| Reaction Time | % hydrolysis | | |
|---|---|---|---|
| | E. coli K12 | E. coli BRL 1873 | Control |
| 0 | 0% | 0% | 0% |
| 3 hours | 27% | 24% | 11% |
| 6 hours | 57% | 50% | 18% |

Assay 2

De-esterification of α-(p-methylphenyl) ester of AB17421 by esterase from *Pseudomonas aeruginosa*

The cultivation and hydrolysis as described in assay 1 were repeated with two strains of *Pseudomonas aeruginosa* (A, NCIB 10110 and R59, NCIB 10111) were grown as in assay 1. The results are given in Table 2.

TABLE 2

| Reaction Time | % hydrolysis | |
|---|---|---|
| | Ps. aeruginosa A | Ps. aeruginosa R59 |
| 0 | 0% | 0% |
| 3 hours | 25% | 22% |
| 6 hours | 51% | 48% |

Assay 3

De-esterification of α-(p-methylphenyl) ester of AB17421 by esterases from *Aspergillus niger* and Saccharomyces SP (a) cultivation of *Aspergillus niger*

*Aspergillus niger* BRL 822 (IMI 130783) was grown up by the surface culture method. The medium consisted of 90% bran extract, 10% mineral salt solution, 4% glucose and 3% ammonium sulphate. The bran extract was prepared by soaking 200 g bran in 1 liter of tap water at 50° C. for 1-2 hours before removing the solids. The salt solution was 0.5% KCl, 0.5% $MgSO_4.7H_2O$, 1% $K_2HPO_4$ and 0.01% $FeSO_4.7H_2O$. 15 g bran and 30 ml of the above medium was placed in each 500 ml flask before autoclaving. The flasks were inoculated with 4 ml of a spore suspension obtained by adding sterile water to an agar slope of *Aspergillus niger*. The agar had the following composition: malt extract (Oxoid), 3 g/l; yeast extract (Oxoid), 3 g/l; bacteriological peptone, 5 g/l; dextrose, 10 g/l; technical agar No. 3 (Oxoid), 20 g/l; the pH was adjusted to 6.8 with KOH. The organism was grown at 26° C. for 5 days without shaking. After growth the flasks of Aspergillus culture were shaken vigorously with 100 ml water for 15 minutes and the cells and solids were then removed by centrifugation and discarded. The supernatant was used as source of enzyme.

(b) Cultivation of Saccharomyces sp.

Two strains of Saccharomyces (*S. cerevisiae* BRL 611 and *S. carlsbergensis* BRL 622) were grown in 500 ml shake flasks containing 100 ml medium at 26° C. The medium consisted of:

1% bacteriological peptone (Oxoid) plus 1% glucose.

(c) Hydrolysis Reactions

The three microbial preparations were each incubated at 1:1 v/v ratio with 8 mg/ml solution of the esters in 0.05 M potassium phosphate buffer. The final concentrations of the microbial preparations were: Aspergillus niger—50% concentration of the water extract; and Saccharomyces—50% concentration of the fully grown culture. The reaction conditions were as in assay 1 using using the α-(p-methylphenyl) ester of AB17421. The percentage of AB17421 formed after 3 hours and 6 hours, determined as in the assay method above, are shown in Table 3.

TABLE 3

| Reaction Time | Aspergillus niger | Saccharomyces cerevisiae | Saccharomyces carlsbergensis |
|---|---|---|---|
| 0 | 5% | 2% | 4% |

TABLE 3-continued

| Reaction Time | Aspergillus niger | Saccharomyces cerevisiae | Saccharomyces carlsbergensis |
|---|---|---|---|
| 3 hours | 91% | 12% | 12% |
| 6 hours | 100% | 16% | 18% |

Assay 4

De-esterification of α-(p-methylphenyl) ester of AB17421 by purified enzymes

The following enzymes were incubated with the ester: bromelain, from pineapple stem (Sigma)*; papain, from papaya latex (Sigma)*; gelatase (A.B.M. Industial Products)*; trypsin 2U/mg (Merck)* and pancreatin (B.D.H.)*.

The concentration of enzyme used in the reaction mixture was 2 mg/ml except for pancreatin which was used as a 1 mg/ml suspension. The reaction conditions were as in assay 2. The percentage hydrolysis results are given in Table 4.

TABLE 4

| Reaction Time | bromelain | papain | gelatase | trypsin | pancreatin |
|---|---|---|---|---|---|
| 0 | 7% | 4% | 4% | 5% | 4% |
| 3 hours | 18% | 28% | 15% | 82% | 28% |
| 6 hours | 29% | 39% | 25% | 94% | 39% |

[*Enzyme sources:

Sigma (London) Chemical Co. Ltd., Fancy Road, Poole, Dorset, England.

A.B.M. Industrial Products Ltd., Woodley, Stockport, Cheshire, England.

E. Merck, D61, Darmstadt, Germany.

B.D.H. Chemicals Ltd., Poole, Dorset, Endland.]

We claim:

1. A process for the preparation of a 6α-methoxy penicillin formula (I):

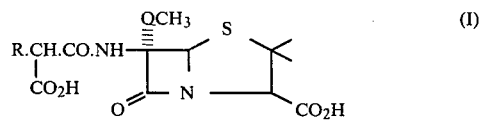

wherein R represents phenyl or 2- or 3-thienyl, which process comprises subjecting a compound of formula (IV):

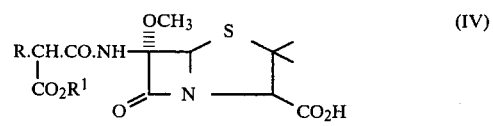

where $R^1$ is an aryl radical, to the action of an enzyme selected from the group consisting of bromelain, papain, gelatase, trypsin, pancreatin and an esterase-producing strain of *Escherichia coli, Pseudomonas aeruginosa, Aspergillus niger,* and *Saccharomyces* sp.

2. A process as claimed in claim 1 wherein $R^1$ is phenyl or substituted phenyl wherein the substituent is at least one of chloro, bromo, fluoro, $C_{1-6}$ alkyl, $C_{1-6}$ alkoxy, $C_{1-6}$ alkanoyl, $C_{1-6}$ alkoxycarbonyl, nitro or di-$(C_{1-6})$ alkylamino.

3. A process as claimed in claim 1 wherein $R^1$ is phenyl, or mono-, di- or tri-$(C_{1-6})$-alkyl substituted phenyl.

4. A process as claimed in claim 1 wherein $R^1$ is phenyl, o-, m-, or p-methylphenyl, ethylphenyl, n- or iso-propyl phenyl, or n-, sec-, iso- or t-butylphenyl.

5. A process as claimed in claim 1 wherein R is 3-thienyl.

6. A process as claimed in claim 1, wherein the esterase-producing strain of microorganism or mold is selected from the group consisting of *Escherichia coli* K 12 (NCIB 10112), BRL 1873 (ATCC 9723), *Pseudomonas aeruginosa* A (NCIB 10110), R59 (NCIB 10111) *Aspergillus niger* BRL 822 (IMI 130783), *Saccharomyces cerevisiae* BRL 611, and *Saccharomyces carlsbergensis* BRL 622.

7. A process as claimed in claim 1 wherein the esterase-producing strain of microorganism is *Aspergillus niger*.

* * * * *